United States Patent [19]

Volk et al.

[11] Patent Number: 5,067,947
[45] Date of Patent: Nov. 26, 1991

[54] SYRINGE PLUNGER ROD MOUNT

[75] Inventors: John F. Volk, Chester Springs, Pa.; Thomas Michaels, Upper Saddle River, N.J.

[73] Assignee: Tri/West Systems, Inc., Upper Saddle River, N.J.

[21] Appl. No.: 381,383

[22] Filed: Jul. 18, 1989

[51] Int. Cl.5 ............................................. A61M 5/24
[52] U.S. Cl. ................................. 604/201; 604/110; 604/193; 604/234
[58] Field of Search ............... 604/110, 201, 226, 228, 604/218, 222, 221, 232, 263, 193, 234

[56] References Cited

U.S. PATENT DOCUMENTS

| | | | |
|---|---|---|---|
| 2,020,828 | 11/1935 | Goldberg | 604/201 |
| 2,728,341 | 11/1955 | Roehr | 604/226 |
| 3,333,682 | 8/1967 | Burke | 604/110 |
| 3,357,427 | 12/1967 | Wittke et al. | 604/226 |
| 3,375,825 | 4/1968 | Keller | 604/201 |
| 3,534,734 | 8/1970 | Budreck | 604/226 |
| 3,783,997 | 1/1974 | Brown | 604/201 |
| 3,820,652 | 6/1974 | Thackston | 604/201 |
| 3,825,003 | 7/1974 | Kruck | 604/201 |
| 4,270,536 | 6/1981 | Lemelson | 604/110 |
| 4,334,536 | 6/1982 | Pfleger | 604/201 |
| 4,430,080 | 2/1984 | Pasquini et al. | 604/263 |
| 4,445,895 | 5/1984 | Margulies | 604/201 |
| 4,781,700 | 11/1988 | Vicario | 604/201 |
| 4,808,169 | 2/1989 | Haber et al. | 604/110 |
| 4,850,968 | 7/1989 | Romano | 604/110 |

FOREIGN PATENT DOCUMENTS

| | | | |
|---|---|---|---|
| 0287950 | 10/1988 | European Pat. Off. | 604/110 |
| 2197792 | 6/1988 | United Kingdom | 604/110 |
| 2210270 | 6/1989 | United Kingdom | 604/110 |

Primary Examiner—C. Fred Rosenbaum
Assistant Examiner—Sharon Finkel
Attorney, Agent, or Firm—Eugene E. Renz, Jr.

[57] ABSTRACT

A syringe device has a vial for medicaments having a first open end at a sealed second end. The first end having a plunger tip for sealing the end and has a finger grip means mounted adjacent the first. The needle and hub is slidably mounted on a needle on the second end in axial alignment with the sealed end to position said needle for access to the vial. The plunger rod has a first engagement on one end for engagement with the plunger tip and mounting means for detachably mounting the plunger between the finger grip and the hub to prevent access to the vial when the plunger is mounted thereon.

9 Claims, 3 Drawing Sheets

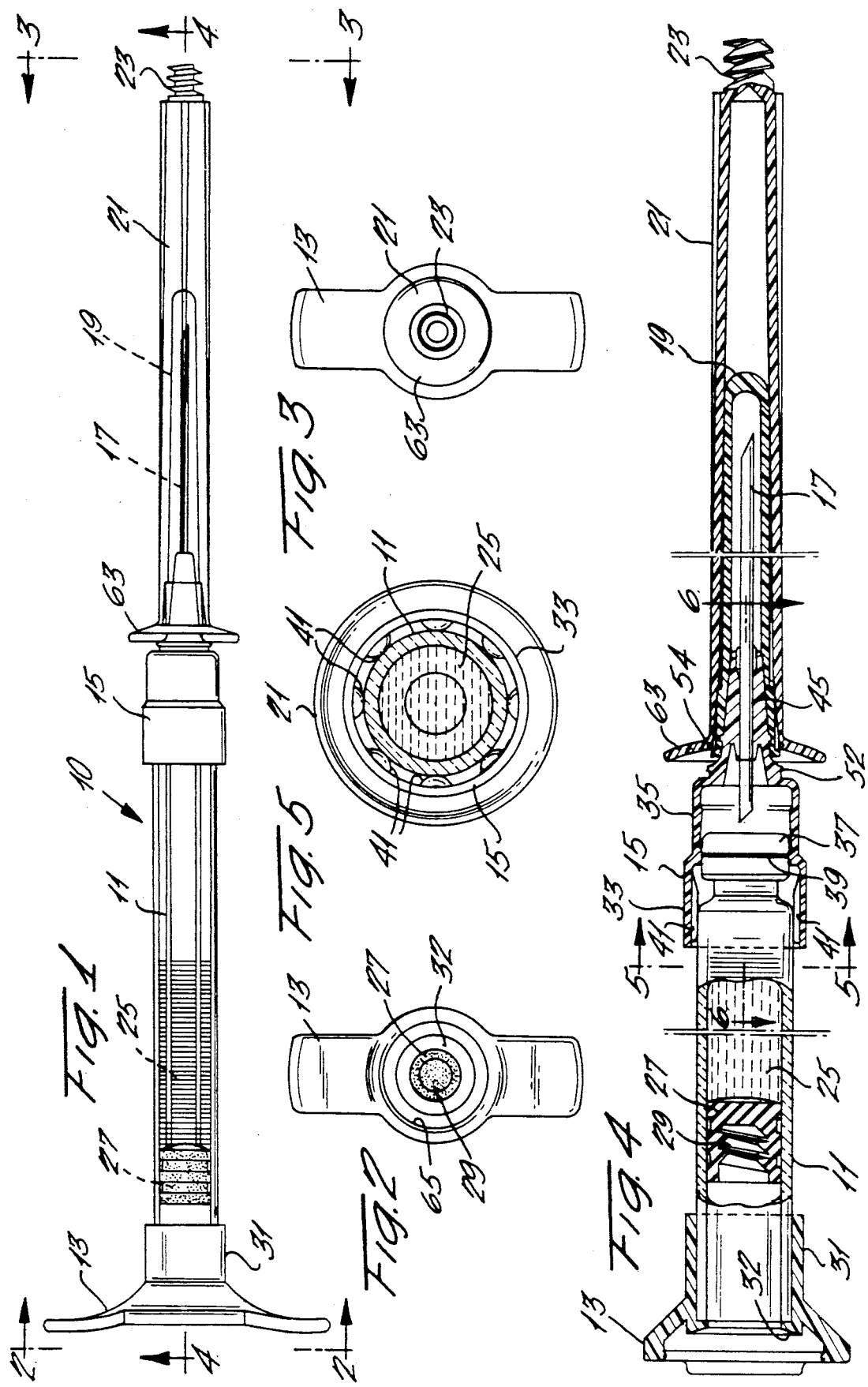

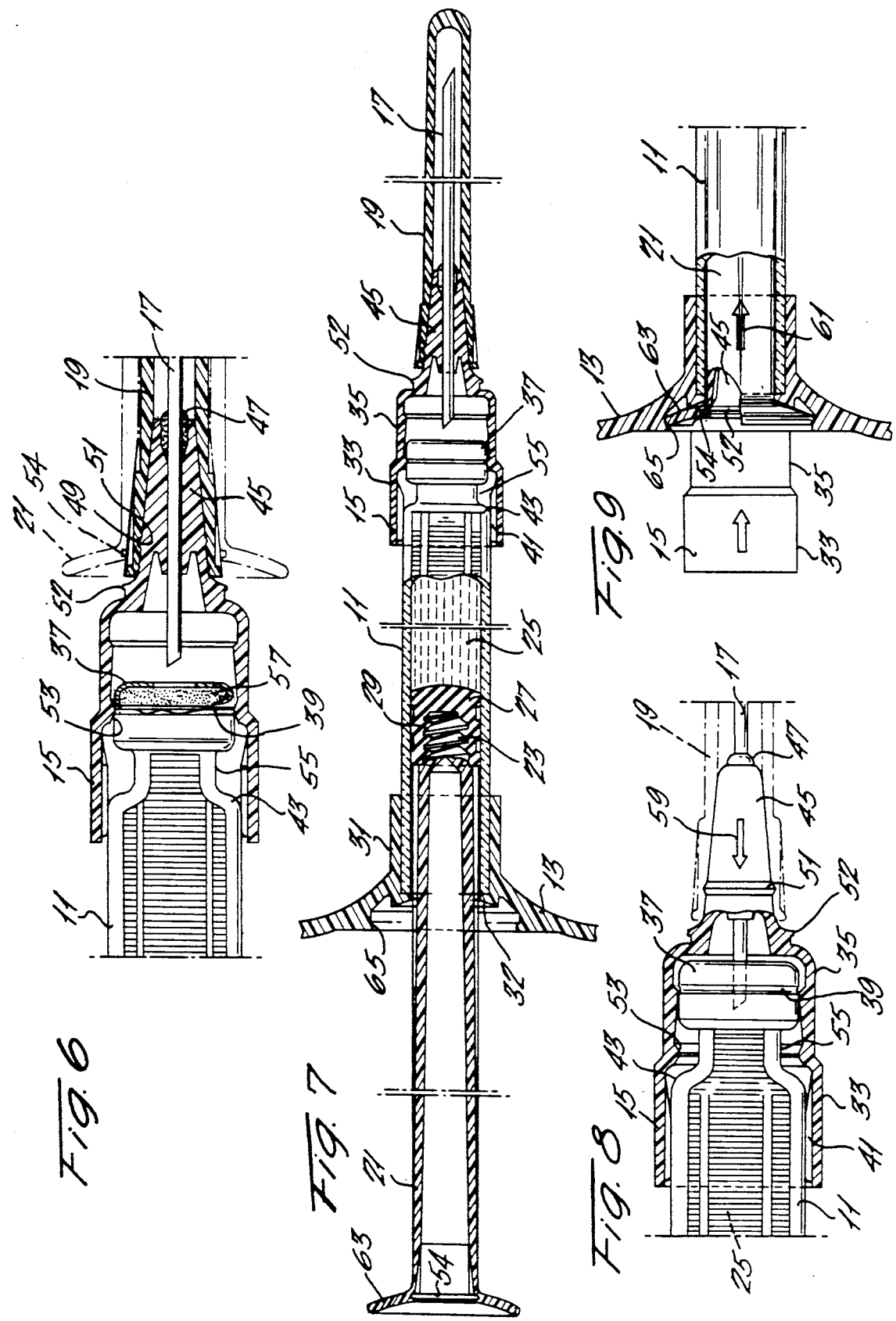

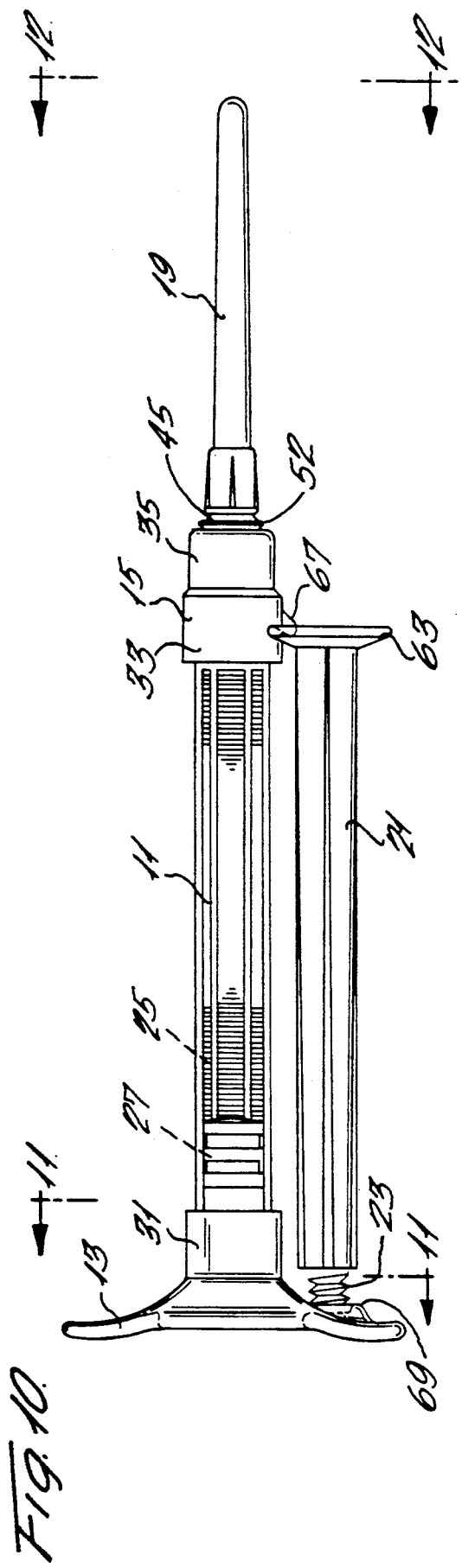
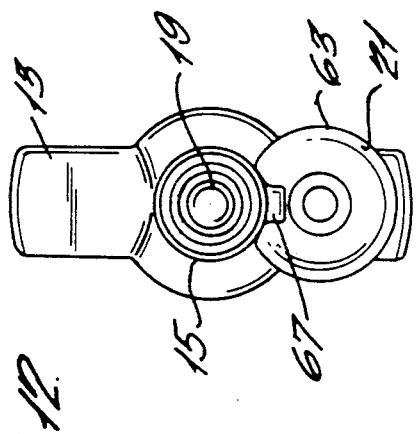
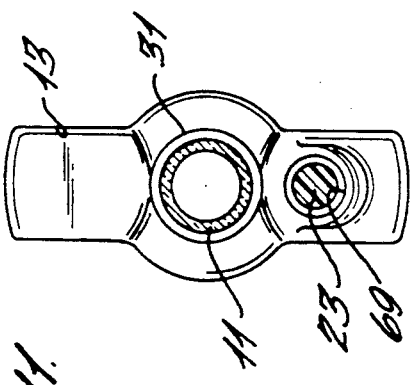

SYRINGE PLUNGER ROD MOUNT

FIELD OF THE INVENTION

The present invention relates to hypodermic syringe assemblies and more specifically to a prefilled disposable syringe assembly for medicament in injectable form.

BACKGROUND OF THE INVENTION

Disposable prefilled syringe assemblies for dispensing parenteral pharmaceuticals by injection are not new per se. Many syringe assemblies have been proposed which employ a glass tube filled with the desired medicaments. At one end of the glass tube is a plunger tip which functions as a seal prior to axial movement of the plunger tip to empty the contents of the syringe. At the other end of the glass tube or vial is a seal, often in the form of a elastomeric disk held in place by a plastic or metal cap. A plunger rod is generally associated with the plunger tip, and in many cases, the plunger tip and plunger rod are not fixedly attached to one another but are assembled at the time of intended use of the syringe assembly. One such device is shown in U.S. Pat. No. 3,967,759.

The needle design which is often times used with disposable prefilled syringe assemblies involves the use of a double ended needle assembly which is attached to the sealed end of the glass vial in a first position where the needle is aligned with but not penetrating the seal. The needle assembly then is movable to a second position whereby the interiorly pointing end of the needle penetrates the seal and provides access to the contents. The other end of the needle which is, of course, the end through which the medicine is administered to the patient, is covered by a needle cover or needle shield. One such design is shown in U.S. Pat. No. 3,739,779.

These and other designs of similar structure are complicated and/or oversized. Other designs have certain functional disadvantages and drawbacks, particularly when a single selfcontained assembly is needed.

None of these patents disclose or suggest a device which is totally suitable as a disposable prefilled syringe assembly. Particularly, none of the prior art provides a compact assembly which is provided with a functional locking mechanism to prevent inadvertent movement or damage to seals at either end of the prefilled container. It would be of great advantage if a syringe assembly could be provided which could be prefilled and stored or transported for a long period of time, followed by quick and efficient use when needed. Accordingly, it is an object of the present invention to provide such a device.

SUMMARY OF THE INVENTION

The above and other objects of the present invention may be achieved in the following manner. Specifically, it has now been discovered that a new and useful syringe device may be provided having the following elements.

The device includes a vial for medicaments and has a first open end and a sealed second end. On the first end, a plunger tip is positioned which seals that end and which, when moved to the other end, will force the contents of the vial out of the device. A finger grip is mounted adjacent to that first end.

The second end of the vial is sealed, preferably using an elastomeric liner mounted on the end with a fitted metal cap. A needle and hub means for slidably mounting a needle on the second end is provided and is in axial alignment with the sealed end so as to position the needle for access to the vial. A plunger rod is provided having a first engagement means on one end for engaging the plunger tip. Preferably, the other end of the plunger rod includes an annular disk suitable for accommodating the thumb as the plunger is depressed to evacuate the syringe device.

Finally, a mounting device is provided for detachably mounting the plunger between the finger grip and the hub means. When the plunger is mounted in this position, the slidably mounted hub and needle cannot move axially to engage the liner seal, thereby preventing access to the contents of the vial while the plunger rod is in the locking position.

In a preferred embodiment, the hub means includes a double ended needle assembly which is axially movable from a first position during which the plunger is detachably mounted to the device and a second position which provides access by the needle to the vial. This is best accomplished in this embodiment providing said hub means with an inwardly facing annular ring and providing the second end of the vial with a pair of annular grooves defining the first and second positions respectively when the annular ring engages those grooves. Those grooves may conveniently be formed by the metal cap or other device used to mount the elastomeric liner which seals the end of the vial.

The device further includes a needle cover or shield which may conveniently be attached to the hub means using an annular ring and groove assembly for snap fitting. The plunger rod may be hollow and axially overlie the needle shield and a portion of the needle end of the syringe. In one particularly preferred embodiment, the plunger rod includes an annular disk which is sized to engage a similar annular opening in the finger grip. The finger grip, of course, has a first annular opening which is sized to permit said plunger rod and said plunger tip to be engaged for use in dispensing the contents of the syringe device. The second annular opening is larger and is sized to receive the annular disk on the plunger when the plunger rod is fully inserted into the vial to completely expel the contents of the syringe. Additionally, a holding means for maintaining the annular disk of the plunger in the second annular opening of the grip means is provided, such as by a snap fit assembly, so that it is at least very difficult to remove the plunger rod once it has expelled the contents of the syringe device. This safety feature is part of the benefits obtained by the use of disposable systems. At least when the snap fit used syringe is picked up in a casual or accidental encounter, it prevents reusing the syringe device in accordance with its design, which is primarily intended for prefilling and disposal after a single use.

BRIEF DESCRIPTION OF THE DRAWINGS

These and other objects of the present invention and the various features and details of the operation and construction thereof are hereinafter more fully set forth with reference to the accompanying drawings, where:

FIG. 1 is a plan view of a prefilled syringe and its associated plunger rod mounting in accordance with this invention;

FIG. 2 is a left hand end view taken on the line 2,2 of FIG. 1 showing certain details of the finger grip portion of the refillable syringe;

FIG. 3 is a right hand end view taken on the line 3,3 of FIG. 1 showing certain details of the hollow plunger rod axially aligned and overlying the needle shield and needle end of the syringe shown in FIG. 1;

FIG. 4 is an enlarged sectional side elevational view with portions of continuous detail removed taken on the line 4,4 of FIG. 1 illustrating details of the syringe and plunger rod shown in FIG. 1;

FIG. 5 is an enlarged transverse sectional view taken on the line 5,5 of FIG. 4 illustrating certain details of the sliding double ended needle hub assembly;

FIG. 6 is an enlarged fragmentary sectional view taken on the line 6,6 of FIG. 4 with the plunger rod shown in dot and dash outline. The plunger rod having been removed prior to attachment to the piston;

FIG. 7 is an enlarged sectional plan view similar to FIG. 4 but showing the plunger rod threadably engaged with the piston prior to use;

FIG. 8 is a fragmentary sectional view similar to FIG. 6 but showing the needle shield in dot and dash outlining having been removed. The slidable double ended needle hub assembly having been activated to arm the syringe;

FIG. 9 is an enlarged fragmentary sectional view of a portion of the finger grip end of the syringe illustrating the interlocking of the plunger rod terminal end within the finger grip member upon completion of stroke;

FIG. 10 is a modification of the prefillable syringe shown in FIG. 1 illustrating the plunger rod mounted in a parallel axially aligned relationship to the prefilled syringe assembly, the plunger rod captured between a socket in the finger grip member and a slot on the slidable double ended needle assembly to prevent premature arming of the syringe to shorten the length of the prefilled syringe package;

FIGS. 11 and 12 are sectional views taken on the lines 11,11 and 12,12 of FIG. 10 showing additional details of the socket and slot retaining means.

DETAILED DESCRIPTION OF THE PREFERRED EMBODIMENT

Referring now to the drawings and particularly to FIGS. 1 through 12 thereof, there is illustrated one embodiment of a disposable prefilled syringe device in accordance with the invention which is generally designated by the reference numeral 10. The syringe device 10 is adapted to be prefilled with any suitable medicament which doctors, veterinarians, and other users of syringes might wish to have readily available and stored over a long period of time. Further, devices filled with pharmaceutical materials in a ideally clean environment such as in a pharmaceutical laboratory cannot be duplicated in the field where prefilled syringes are often times needed. Thus refilling the device in the field presents additional risk to the patients and, accordingly, the units are normally disposable.

The syringe device 10 of the present invention includes a glass vial or cartridge 11 which has a finger grip 13 mounted on one end and a hub 15 for mounting a needle 17 on the other end. Typically, the needle 17 will have a needle shield 19. In an alternative embodiment, the hub 15 might include a Luer cap and Luer lock.

Also provided as part of the device generally is a hollow plunger rod 21 which is fitted with a threaded end 23. As will be described hereinafter, the end of the vial 11 having the hub 15 is sealed prior to use. The contents 25 are kept in the vial 11 by a plunger tip 27 which effectively seals the other end of the vial 11. The plunger tip will usually be made from a particular formulation which the pharmaceutical manufacturer knows is compatible with the medicament 25. A preferred material is manufactured from an extremely stable elastomeric material and is designated 4416/50 grey, manufactured by The West Company. The plunger tip 27 is also fitted with threads 29 for engagement with the threads 23 of the plunger rod 21.

The finger grip 13 is slidably mounted onto the tube 11 by a base 31 which may also include ring 32 to prevent movement of the finger grip 13 too far down the tube 11. At the other end of the tube 11, shown in section in FIG. 4, is a larger skirt 33 which forms a part of the needle hub means 15 which mounts the needle 17. The hub 15 has a tube engaging portion 35 which is sized to engage the metal cap 37 which secures a rubber liner to seal the end of the tube, as will be described hereinafter. The metal cap 37 has an annular groove 39 of slightly smaller diameter than the diameter of the cap 37. The skirt 33 also has a plurality of projections 41 which support the skirt 33 on the outside diameter of the glass vial 11.

As shown in FIGS. 6 and 8, the needle assembly includes a double ended needle 17 which is held in place by a needle mount 45 and a sealing element 47. The needle shield 19 is maintained in place on the needle mount 45 by an annular groove 49 and an annular ridge 51. In FIG. 6, the annular groove 49 is in the needle shield 19 and the annular ridge 51 is located on the needle shield 19. The groove 49 and ridge 51 allow for a snap fit of the needle cover 19 to protect the needle prior to use.

Needle hub 15 also includes an internal annular ridge 53 which is positioned to cooperatively fit in annular groove 39 when the needle 17 is in a first position in axial alignment with the vial 11 but not penetrating the rubber seal 57 which is held by the metal cap 37 on the end of the glass vial 11. The glass vial end terminates in a neck portion 43 which defines a second groove 55 as is shown in FIGS. 6 and 8. When the needle 17 is in the storage position, as shown in FIG. 6, the annular ridge 53 is firmly positioned in groove 39. When the device becomes operational, the needle 17 is moved in the direction of arrow 59 and penetrates the elastomeric seal 57 which is held by the metal cap 37. The annular ridge 53 then becomes positioned in the region or groove 55 on the neck 43 of the vial 11, thereby locating the needle hub in an active position.

Before the needle 17 has penetrated the elastomeric seal 57 to provide access to the contents 25 of the vial 11, the hollow plunger rod 21 is attached to the plunger tip 27 by threading the end 29 into threads 23 and providing for a positive engagement of the plunger tip 27 and plunger rod 21. The syringe is then ready to operate after the needle shield 19 is removed. The groove 49 and ridge 51 separate easily and the needle shield 19 can be saved to reshield the needle after use.

In one embodiment, the plunger rod 21 contains a hollow portion, such as shown in FIG. 7, which is sized so that the hub 15 with the needle 17 can be inserted into the hollow portion without the shield 19. The hub 15 with the needle 17 can be inserted into the hollow portion without the shield 19. The hub 15 as seen in FIG. 6, has an annular ring 52 which fits inside ridge 54 of plunger rod 21, and this snap fit prevents removal of the hub and keeps the needle from being reused. Ring 52 and ridge 54 are an additional safety feature.

The plunger tip 27 will expel all of the contents 25 from the vial 11 when the plunger rod 21 is inserted all the way into the vial 11, as shown in FIG. 9 by arrow 61. Plunger rod 21 includes a radially extending annular disk 63 which allows the thumb to exert steady pressure on the plunger rod 21. When the plunger rod is fully extended into the glass vial 11, as shown in FIG. 9, the annular disk 63 fits inside the finger grip 13 and snap fits past the annular ridge 65, thereby locking the plunger rod 21 inside the vial 11. Thus, since the syringe device is intended to be disposable after one use, the plunger rod cannot be withdrawn without great difficulty. This safety factor reduces the likelihood of the syringe device being reused even inadvertently by those who temporarily forget that the device is to be disposed of after a single use.

In a preferred embodiment, shown in FIG. 10, the plunger rod 21 is mounted by a mounting means on the syringe itself. This mounting means includes a groove or lip 67 which is aligned to mate with the annular disk 63 of plunger rod 21. Similarly, the slot 69 is located on the finger grip 13 to accommodate the threaded end 23 of plunger rod 21. When the plunger rod 21 is in place as shown in FIG. 10, the hub 15 is in its first position, as shown in FIG. 6, where the two way needle 17 has not yet penetrated the elastomeric seal 57. If desired, the groove 67 or the slot 69 can be tack welded to the plunger rod 29 by the application of localized heat. In this manner, the plunger rod is locked onto the syringe itself and the two way needle cannot penetrate the elastomeric membrane of the syringe device.

After the completely assembled unit has left the factory in this condition, it is tamper-evident as well as secure. As long as the plunger rod 21 remains fixedly attached to the finger grip 13 and the skirt 33 of hub 15, the contents 25 are secure. When it is time to use the disposable prefilled syringe, the plunger rod 21 is removed from the mounting means by pulling annular disk 63 out of groove 67 and removing the threaded end 23 from the slot 69. The threaded end 23 is then threaded onto threads 29 of plunger tip 23. The hub assembly 15 is depressed so that ridge 53 is removed from annular groove 39 and enters into the neck area 55 of the vial 11. During this time, the interior end of needle 17 punctures the elastomeric seal 57, permitting access to the contents. The device is then ready for use to inject the desired medicament into the patient or IV system such as a heparin lock. By pressing the plunger rod 21 all the way into the glass vial 11, the annular disk 63 snaps past annular ridge 65, thereby preventing reuse of the syringe. The device is now ready for proper disposal.

The device of this invention is compact and has a much shorter package size. This permits the use of the device in hospital carts and the like which have limited drawer length. When the device is used, insertion of plunger rod 21 into vial 11, and insertion of hub 15 and needle 17 into plunger rod 21, as shown in FIG. 9, permits safe disposal thereof.

While particular embodiments of the present invention have been illustrated and described herein, it is not intended to limit the invention and changes and modifications may be made therein within the scope of the following claims.

What is claimed is:
1. A syringe device, comprising;
    a vial for medicaments having a first open end and a penetratable seal at its opposite second end;
    finger grip means mounted adjacent said first end;
    needle hub means for mounting a needle on said second end in axial alignment with said seal actuatable axially between an unarmed position spaced from said seal and an armed position penetrating said seal to access contents of said vial;
    an elongated plunger rod;
    mounting means for mounting said plunger rod between said finger grip and needle including a fracturable detachable connection of said plunger rod to said hub means operable to normally prevent axial displacement of said hub means to said armed position and upon fracturing of said connection permitting arming and providing visual indicia of breaking of said connection;
    said hub means including a double ended needle assembly axially movable from a first position for detachably mounting said plunger with said mounting means and the second position when said plunger is removed to thereby provide access by said needle to said vial.
2. The device of claim 1, wherein said second end sealing means is an elastomeric liner fitted over said end.
3. The device of claim 2, wherein said elastomeric liner is mounted on said second end with a metal cap.
4. The device of claim 1, wherein said hub means includes an inwardly facing annular ring and said second end includes a pair of annular grooves locating said first and said second positions respectively when said ring engages each of said grooves.
5. The device of claim 1, wherein said needle is fitted with a needle cover.
6. The device of claim 5, wherein said needle cover and said hub means include an annular ring and groove assembly for snap fitting said needle cover on said hub.
7. The device of claim 5, wherein said plunger rod includes a hollow axially centered portion sized to frictionally fit said needle cover.
8. A syringe device as claimed in claim 1 including means defining a cavity in an annular rib in said finger grip means and said plunger rod having a radially outwardly directed disk portion which is sized to snap fit into said cavity behind said rib when the plunger rod is actuated to said final discharge position.
9. A syringe device as claimed in claim 1 wherein said plunger rod has first locking means located adjacent its open end and said needle hub means has complementary second locking means whereby a spent needle can be inserted interiorally of the plunger rod and locking means and said locking means interengaged to safely hold the spent needle in place in the plunger rod.

* * * * *